United States Patent [19]

Deur et al.

[11] Patent Number: 4,549,026

[45] Date of Patent: Oct. 22, 1985

[54] PROCESS FOR THE PREPARATION OF CONDENSED TRIAZOLES

[75] Inventors: Michel Deur, Mulhouse, France; Istvan Toth, Bottmingen, Switzerland

[73] Assignee: Sandoz Ltd., Basel, Switzerland

[21] Appl. No.: 353,872

[22] Filed: Mar. 2, 1982

[30] Foreign Application Priority Data

Mar. 6, 1981 [DE] Fed. Rep. of Germany ....... 3108405

[51] Int. Cl.⁴ .................. C07D 249/18; C07D 249/20
[52] U.S. Cl. .................................................. 548/257
[58] Field of Search ............................. 548/257, 260

[56] References Cited

U.S. PATENT DOCUMENTS

| | | | |
|---|---|---|---|
| 3,227,726 | 1/1966 | Levy | 548/257 |
| 3,564,001 | 2/1971 | Long | 548/257 |
| 3,639,431 | 2/1972 | Mcteer et al. | 548/257 |
| 3,983,132 | 9/1976 | Strobel | 548/260 |
| 4,041,044 | 8/1977 | White et al. | 548/257 |
| 4,086,242 | 4/1978 | Diehl | 548/257 |

FOREIGN PATENT DOCUMENTS

| | | | |
|---|---|---|---|
| 776680 | 1/1968 | Canada | 548/257 |
| 1581407 | 12/1980 | United Kingdom | 548/257 |

OTHER PUBLICATIONS

Sieper, Helmuth, *Chem. Ber.*, vol. 100, pp. 1646-1654, (1967).

Noller, Carl, *Textbook of Organic Chemistry*, p. 126, (1966).

Rochat, Claude, Condensed Triazoles Chem. Abst. 90: 103965f.

*Primary Examiner*—Donald G. Daus
*Assistant Examiner*—G. Hendricks
*Attorney, Agent, or Firm*—Gerald D. Sharkin; Richard E. Vila; Frederick H. Weinfeldt

[57] ABSTRACT

A process for the preparation of condensed triazoles of formula I

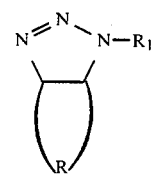

in which R together with the triazole group form an aromatic group $R_1$ is hydrogen or a hydrocarbon group the process comprising
reacting in a medium containing an organic phase a compound of formula II

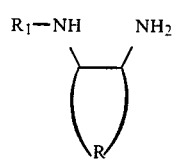

with a nitrite and an acid.

The reaction is preferably carried out at a raised temperature.

23 Claims, No Drawings

PROCESS FOR THE PREPARATION OF CONDENSED TRIAZOLES

The invention relates to a process for the preparation of a condensed triazole of the formula I

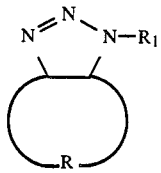

in which R together with the carbon atoms to which R is attached forms a group of aromatic character and
$R_1$ is hydrogen or a hydrocarbon group,
the process comprising
reacting a compound of formula II

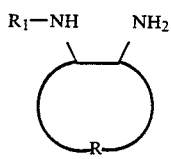

where R and $R_1$ are above defined, an inorganic nitrite and an acid in a medium comprising an organic phase.

The preferred molar ratios are 1 mole of the compound of formula II, one mole of nitrite and at least one mole of acid.

Preferably, the organic phase includes a solvent other than the acid. In this case preferably the acid is added to the nitrite and the compound of formula II.

Further according to the invention there is provided a process for the preparation of a compound of formula I, as defined above, comprising
reacting a compound of formula II, as defined above, an inorganic nitrite and an acid in a two phase system, one phase being an organic phase and the other phase being an aqueous phase, and
separating the organic phase containing the compound of formula I, as defined above, from the aqueous phase containing inorganic salt and other impurities.

Desirably the two phases are substantially mutually insoluble. It is also desirable for the two phases to be easily separable.

It has been found that when two such phases form, the compound of formula I, especially a benzotriazole, will be more soluble in the organic phase than in the aqueous phase whereas unwanted impurities mainly remain in the aqueous phase.

Preferably R together with the carbon atoms to which R is attached form a benzotriazole group. The group R may be substituted with up to four substituents $R_2$ selected from $C_{1-4}$alkyl, $C_{1-4}$alkoxy, phenyl, $C_{6-12}$alkaryl, $C_{6-12}$aralkyl, phenoxy, $C_{6-12}$aralkoxy, $C_{6-12}$alkaroxy and halogen. Preferably $R_2$ is $R_2'$ where $R_2'$ is halogen, preferably chlorine or $C_{1-4}$alkyl, preferably methyl.

Preferably $R_1$ is hydrogen, $C_{1-4}$alkyl, phenyl, $C_{6-12}$aralkyl and $C_{6-12}$alkaryl, more preferably hydrogen, methyl, phenyl and phenyl substituted by one $C_{1-4}$alkyl group.

Preferred compounds of formula I are benzotriazoles, preferably unsubstituted benzotriazole or benzotriazoles substituted by one methyl group (the tolyltriazoles).

The reaction is preferably carried out at a temperature of up to 80° C., preferably 20°-80° C., more preferably in the range 60°-70° C. As the reaction is exothermic this must be carried out with cooling.

The reaction is preferably carried out in a solvent selected from $C_{1-12}$alcohol or an aromatic solvent such as toluene or xylene (or a mixture of xylenes). More preferred solvents are methanol, isopropanol, a $C_{4-12}$alcohol, toluene or xylene. Most preferably the organic solvent is a $C_{4-12}$alcohol, toluene or xylene.

The acid used in the reaction is preferably selected from sulphuric acid, phosphoric acid, hydrochloric acid, an alkali or alkaline earth metal bisulphate, a $C_{1-4}$alkanoic acid, oxalic acid, benzoic acid or phthalic acid. More preferred acids are sulphuric acid, sodium or potassium bisulphate, phosphoric acid, $C_{1-4}$alkanoic acid, especially acetic acid. Most preferably the acid is sulphuric acid. Excess of an alkanoic acid, especially acetic acid, may also be used as a solvent for the reaction and may replace other solvents. When the acid is the solvent the nitrite is preferably added, portionwise, to the reaction mixture as the final reactant.

Preferably the nitrite is an alkali metal nitrite, more preferably sodium or potassium nitrite.

The presence of water does not affect the reaction, indeed the reaction produces 2 moles of water per mole of reacted diamine.

Preferably the compound of formula II is of the formula IIa

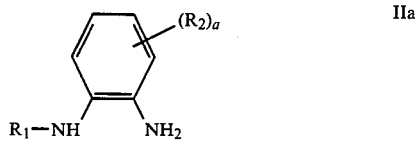

where $R_1$ and $R_2$ are defined above and
a is 0 to 4, preferably 0 or 1.

More preferably the compound of formula II is selected from o-phenylene diamine, mono-, di- or trichloro- or methyl-ortho-phenylene diamine (preferably monochloro-ortho-phenylene diamine) or orthodiaminotoluene. Other diamines that can be used in a process of the invention are 3,3'4,4'-tetraamino diphenyl alkanes, particularly where the alkane is methane and accordingly the compound of formula I produced will be of the formula

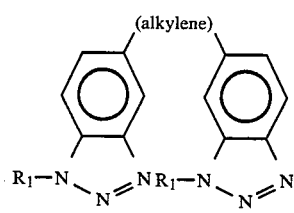

The condensed triazoles prepared according to the invention are useful as anticorrosion agents and as U.V. stabilisers.

In the following Examples all percentages and parts are by weight and all temperatures are in degrees Centigrade unless indicated to the contrary.

EXAMPLE 1

108 Parts of ortho-phenylene diamine and 71 parts of sodium nitrite are suspended in 400 parts of xylene isomer mixture; the suspension is warmed to 30°–35° and then 72 parts of glacial acetic acid are added over 2½ hours with good stirring and the temperature is kept in the region of 25°–35° with cooling.

After the acid has been added the mixture is heated, whilst stirring, for 30 minutes at 50° and then 55 parts of methanol and 20 parts of activated charcoal are added, after which the mixture is stirred for 30 minutes, filtered and the residue is washed with 35 parts of methyl alcohol warmed at 40°. The methylalcohol is distilled off under vacuum at 65°.

With good stirring and by seeding the xylene solution, containing the benzotriazole, the reaction product crystallises out at 35°–40°. The benzotriazole is filtered and the residue is first washed with 20 parts of cold xylene isomer mixture and then with 100 parts of cold water and is then dried under vacuum at 65°.

Instead of using ortho-phenylene diamine an equivalent molar amount of 3- or 4-methyl ortho-phenylene diamine or 3- or 4-chloro-ortho-phenylene diamine can be used in the method of this Example. Further instead of the xylene mixture toluene may be used as the solvent.

EXAMPLE 2

According to the method of Example 1, 72 parts of glacial acetic acid is added to 108 parts of ortho-phenylene diamine, 235 parts of methanol and 71 parts of sodium nitrite. The mixture is warmed to 70°–80° and 160 parts of methanol are distilled off, the residual solution is then treated with 100 parts of cold water and 15 parts of activated charcoal. The temperature is then reduced to about 60°, stirred for 30 minutes at this temperature, clear filtered and the residue is washed in 20 parts of water. The filtrate is then poured into 400 parts of ice/water mixture (300 parts ice to 100 parts water) and the reaction product is precipitated out.

To complete the precipitation 80 parts of sodium chloride are stirred into the mixture, the product is then filtered and vacuum dried.

EXAMPLE 3

According to Example 1, 70 parts of approximately 99% acetic acid are added to 122 parts of 3,4-diaminotoluene, 1000 parts of toluene and 71 parts of sodium nitrite and after the reaction is completed the mixture is heated to 50° whilst stirring, treated with 25 parts of activated charcoal and stirred for a further 30 minutes. After this the undissolved sodium acetate crystals and activated charcoal are filtered off and the filtrate is concentrated by evaporation. The residue is a tolyltriazole in a yield of about 99% of theory.

EXAMPLE 4

According to the method of Example 1, 102 parts of 50% sulphuric acid are slowly added to 122 parts of ortho-diaminotoluene (isomer mixture), 72 parts of sodium nitrite and 200 parts of isopropanol at 70° whilst stirring. The mixture is stirred for 1 hour and the resulting sodium sulphate (which is partially hydrated) is filtered off and the salt free solution so produced is concentrated by evaporation. The residue is a crude tolyltriazole having a yield of 99% of theory.

EXAMPLE 5

According to the method of Example 1, 200 parts of 50% phosphoric acid are added to 122 parts of ortho diaminotoluene (isomer mixture), 72 parts sodium nitrite, 200 parts of n-butanol and 32 parts of water. The mixture is then stirred for 1 hour at 80°. Two layers form, an organic and an aqueous layer, and the aqueous layer containing the dissolved sodium phosphate is then separated from the organic layer. From the organic layer n-butanol is then distilled off and the residue is crude tolyltriazole having a yield of 98% of theory.

EXAMPLE 6

According to Example 1, 120 parts of 30% hydrochloric acid are slowly added to 142.5 parts of chloro-ortho phenylene diamine (isomer mixture), 72 parts of sodium nitrite, 200 parts of octylalcohol and 50 parts of water. The mixture is then stirred for 1 hour at 60°. Two layers form, an organic layer and an aqueous layer.

The aqueous layer containing sodium chloride is separated off and, from the organic layer, octylalcohol is recycled under vacuum distillation. The residue is crude chloro-benzotriazole having a yield of 97% of theory.

EXAMPLE 7

62 Parts of sodium bisulphate and 36 parts of sodium nitrite are slowly added portion by portion whilst stirring to a solution of 61 parts ortho-diaminotoluene (isomer mixture) and 120 parts methanol. The reaction is then heated to boiling and stirred under reflux for 1 hour. The resulting sodium sulphate is filtered off and 500 parts water and 20 parts activated charcoal are added to the salt free methanol solution. The mixture is refluxed for 30 minutes, hot filtered and the residue is washed with 40 parts of hot water. From the filtrate methanol is distilled off, the remaining aqueous solution is cooled and is seeded with tolyltriazole and allowed to crystallise and the resulting tolyltriazole is filtered. After vacuum drying a pure colourless tolyltriazole isomer mixture having an 85.6% yield of theory results. The last (aqueous) filtrate can be further treated to improve the yield of tolytriazole formed.

What is claimed is:

1. A process for the preparation of a condensed triazole of the formula I

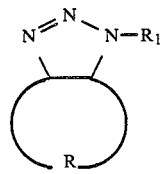

in which
R together with the carbon atoms to which R is attached forms a group of aromatic character and
$R_1$ is hydrogen or a hydrocarbon group, the process comprising reacting at up to 80° C., under cooling, a compound of formula II

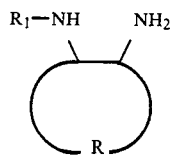

where
R and $R_1$ are above defined,
an inorganic nitrite and an acid in a two phase system, one phase being an organic solvent phase and the other phase being an aqueous phase, and
separating the organic phase containing the compound of formula I, as defined above, from the aqueous phase.

2. A process according to claim 1 in which the organic solvent is a $C_{4-12}$ alcohol, toluene or xylene.

3. A process according to claim 1 in which the acid is added to the compound of formula II, and the nitrite.

4. A process according to claim 1 in which the nitrite is sodium or potassium nitrite.

5. A process according to claim 1 in which the acid is sulphuric acid, sodium or potassium bisulphate, phosphoric acid or $C_{1-4}$ alkanoic acid.

6. A process according to claim 1 in which the reaction is carried out in the temperature range 60°–70° C.

7. A process according to claim 1 in which the compound of formula I is a benzotriazole.

8. A process of claim 1 in which the molar ratios are one mole of the compound of formula II, one mole of nitrite, and at least one mole of acid.

9. A process of claim 1 in which the group R may be substituted with up to four substituents $R_2$ each of which is independently selected from the group consisting of $C_{1-4}$ alkyl, $C_{1-4}$ alkoxy, phenyl, $C_{6-12}$ alkaryl, $C_{6-12}$ aralkyl, phenoxy, $C_{6-12}$ aralkoxy, $C_{6-12}$ alkaroxy, and halogen.

10. A process of claim 1 in which $R_1$ is selected from the group consisting of hydrogen, $C_{1-4}$ alkyl, phenyl, $C_{6-12}$ aralkyl, and $C_{6-12}$ alkaryl.

11. A process of claim 9 in which $R_1$ is a member of the group consisting of hydrogen, methyl, phenyl and phenyl substituted by one $C_{1-4}$ alkyl group.

12. A process of claim 1 in which the reaction is carried out at from 20° to 80° C.

13. A process of claim 1 in which the acid is acetic acid.

14. A process of claim 1 in which the acid is sulfuric acid.

15. A process of claim 9 in which the compound of formula II is of the formula IIa:

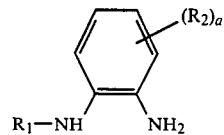

in which
$R_1$ is hydrogen $C_{1-4}$ alkyl, phenyl, $C_{6-12}$ aralkyl or $C_{6-12}$ alkaryl;
$R_2$ is as defined in claim 9 and a is 0 to 4.

16. A process of claim 1 in which the compound of formula II is selected from the group consisting of o-phenylene diamine, mono-, di- and tri-chloro- and methyl-ortho-phenylene diamine.

17. A process of claim 15 in which a is 0 or 1.

18. A process of claim 2 in which the inorganic nitrite is an alkali metal nitrite.

19. A process of claim 18 in which the alkali metal nitrite is sodium or potassium nitrite.

20. A process according to claim 17 in which $R_1$ is hydrogen and $R_2$ is chloro or methyl.

21. A process according to claim 18 in which the acid is sulphuric acid, phosphoric acid, hydrochloric acid, an alkali or alkaline earth metal bisulphate, a $C_{1-4}$ alkanoic acid, oxalic acid, benzoic acid or phthalic acid.

22. A process according to claim 21 in which the compound of formula II is ortho-phenylene diamine, mono-chloro-ortho-phenylene diamine or monomethyl-ortho-phenylene diamine.

23. A process according to claim 22 wherein the reaction is effected at 60°–70° C.

* * * * *